United States Patent [19]

Caselgrandi et al.

[11] Patent Number: 4,542,749
[45] Date of Patent: Sep. 24, 1985

[54] SYRINGE FOR USE IN HYPODERMIC BIOPSY, FEATURING AUTOMATIC PLUNGER-RETURN

[76] Inventors: Ivo Caselgrandi, c/o Gardipatent-605, Via Giardini-Palazzo Pororci; Beniamino Palmieri, 45, Via Boito, both of, 41100 Modena, Italy

[21] Appl. No.: 428,115

[22] Filed: Sep. 28, 1982

[30] Foreign Application Priority Data

Sep. 30, 1981 [IT] Italy .................. 40090 A/81

[51] Int. Cl.⁴ .................................. A61M 5/00
[52] U.S. Cl. .......................... 128/752; 604/203; 604/196; 128/763
[58] Field of Search ............ 128/749, 752, 758, 760, 128/763, 765, 764; 604/140, 141, 143, 146, 147, 135, 197, 203, 218, 231, 194–196

[56] References Cited

U.S. PATENT DOCUMENTS

| | | | |
|---|---|---|---|
| 2,490,447 | 12/1949 | Lockhart | 604/203 |
| 2,512,882 | 6/1950 | Truesdale | 604/196 X |
| 3,739,780 | 6/1973 | Ogle | 604/203 |

FOREIGN PATENT DOCUMENTS 2125041 11/1972 Fed. Rep. of Germany ...... 604/203

*Primary Examiner*—Edward M. Coven
*Attorney, Agent, or Firm*—Browdy and Neimark

[57] ABSTRACT

A syringe for hypodermic biopsy featuring automatic plunger-return is set forth herein. It comprises a cylindrical body (1) furnished with a central cylindrical chamber (9)—the latter surrounded by an annular cavity (8)—inside which a plunger (13) consisting of two coaxial cylindrical bodies (14 and 15) with respective fore-end seals (19 and 20) is caused to slide, and in so doing create a fluid/airtight seal; the inner cylindrical body (15) of said plunger (13) carrying the moving core (6) of a hypodermic needle (7) should this be employed to the end of impeding entry into the latter of foreign bodies. Automatic return of the plunger (13) is produced either by expansion of the air compressed within said annular chamber (8) by outer seal (19) during the plunger's (13) forward stroke, or by introduction from without of pressurized fluid into said annular chamber via an entry hole (22), or alternatively, by fitting a spring (21) to the fore-end of said plunger outer cylinder (14), thereby dispensing with the seal (19).

5 Claims, 5 Drawing Figures

SYRINGE FOR USE IN HYPODERMIC BIOPSY, FEATURING AUTOMATIC PLUNGER-RETURN

FIELD OF THE INVENTION

The invention relates to a syringe for carrying out biopsies which incorporates automatic plunger-return—that is, a hypodermic syringe designed for the extraction of organic tissue or fluid samples from the body of a patient to the end that they may be subsequently analysed.

BACKGROUND OF THE INVENTION

The prior art embraces normal hypodermic syringes which may be employed in biopsy by fitting either an ordinary hypodermic needle, or one incorporating a moving core or similar device.

Whether or not an X-ray viewer is being used at the same moment, the biopsy is carried out in two stages: first, the needle—duly attached to the hypodermic syringe—is inserted into the tissue wherefrom a sample is required for analysis, this normally being the work of one hand only; and second, drawing in the minute particles or droplets of fluid, by suction, of or from such tissue as is to be analysed. This operation calls for the use of both hands, in order to hold needle-and-syringe steady with one, and draw out the syringe's moving part, or plunger, with the other—duly creating the vacuum which causes said tissue particles or fluid for analysis to be sucked through the needle. If, for the purposes of a particular biopsy, the necessity arises for maintaining surrounding tissue in a stable posture during extraction of the sample therefrom, then two persons will need to perform the operation, one manipulating the actual hypodermic syringe, the other holding said surrounding tissue steady—as would be the case, for instance, in a mammary biopsy.

SUMMARY OF THE INVENTION

The prior art thus outlined stands in need of further improvement with regard to the possibility of a syringe's being manoeuvred with one hand only, even during the stage in which a tissue-sample is being extracted for the purpose of analysis—thus affording the opportunity for one person only to carry out the biopsy, whatever the circumstances.

From the foregoing preamble one may discern the need for a solution to the technical problem posed by a hypodermic syringe for biopsy purposes which may be manipulated safely with one hand only both during the needle's insertion, and during drawing out of the tissue-sample required for analysis; said facility being afforded utilizing ordinary hypodermic needles with or without a moving core.

The invention solves the technical problem aforesaid by adopting a suitable plastic, glass or metal syringe accepting ordinary hypodermic needles—with or without a moving core—and consisting of a cylindrical body provided with a central cylindrical cavity surrounded by an annular cavity, inside which a plunger is located in fluid/air-tight fashion and caused to slide thus, said plunger comprising two coaxial cylindrical bodies and furnished at one end with a seal; the internal of the two cylindrical plunger bodies carrying the hypodermic needle's moving core whose function is that of impeding entry of foreign bodies into the needle proper.

Advantages afforded by the invention are as follows: facility of laying hold on the syringe with one hand only, both during insertion thereof, and during drawing out of the tissue-sample required for analysis;

automatic syringe-plunger movement during the suction stage;

obviation of the need for a second pair of hands during those biopsies in which there may be a necessity for maintaining tissue in a stable posture about the area of the needle's insertion.

BRIEF DESCRIPTION OF THE DRAWINGS

A number of embodiments of the invention will now be described, strictly by way of example, with the aid of the four accompanying sheets of drawings, wherein.

DESCRIPTION OF PREFERRED EMBODIMENTS

Figure 1:
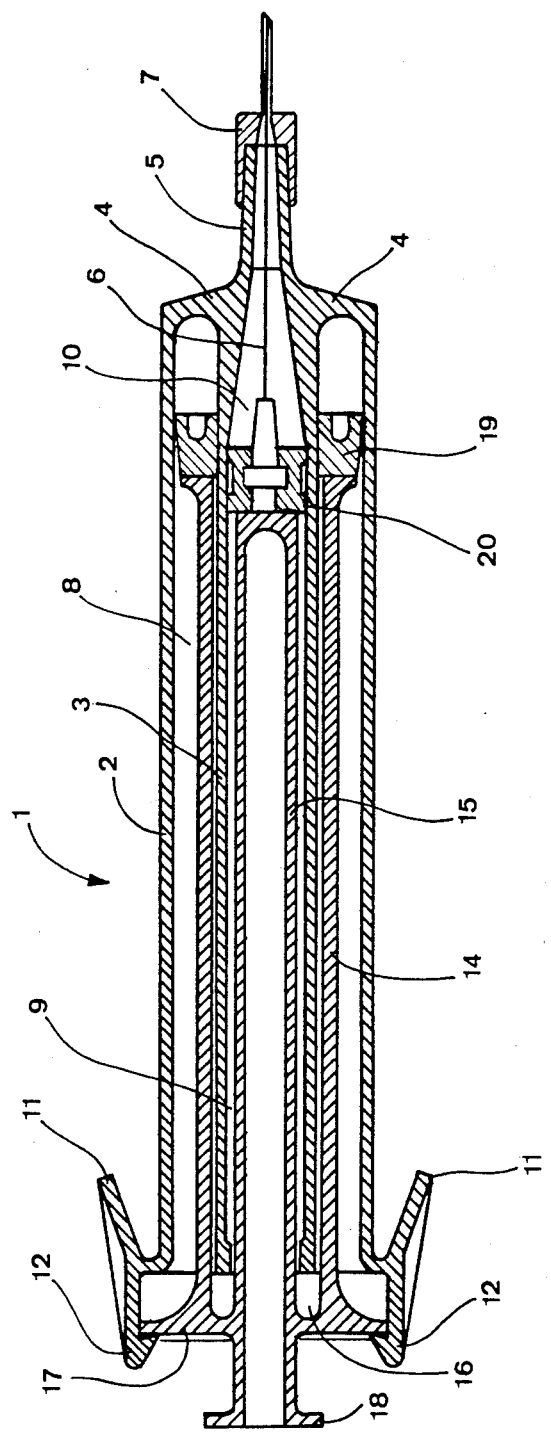
FIG. 1 is the longitudinal, axial section through a complete hypodermic syringe of the type to which the invention relates.
Figure 2:
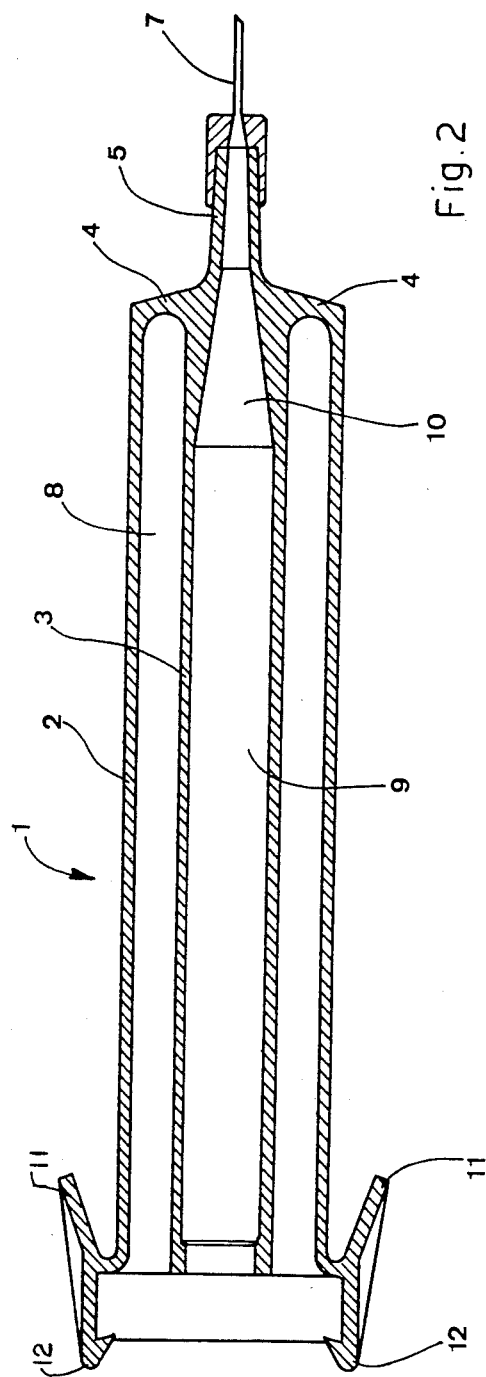
FIG. 2 is a longitudinal and axial section through the syringe body.
Figure 3:
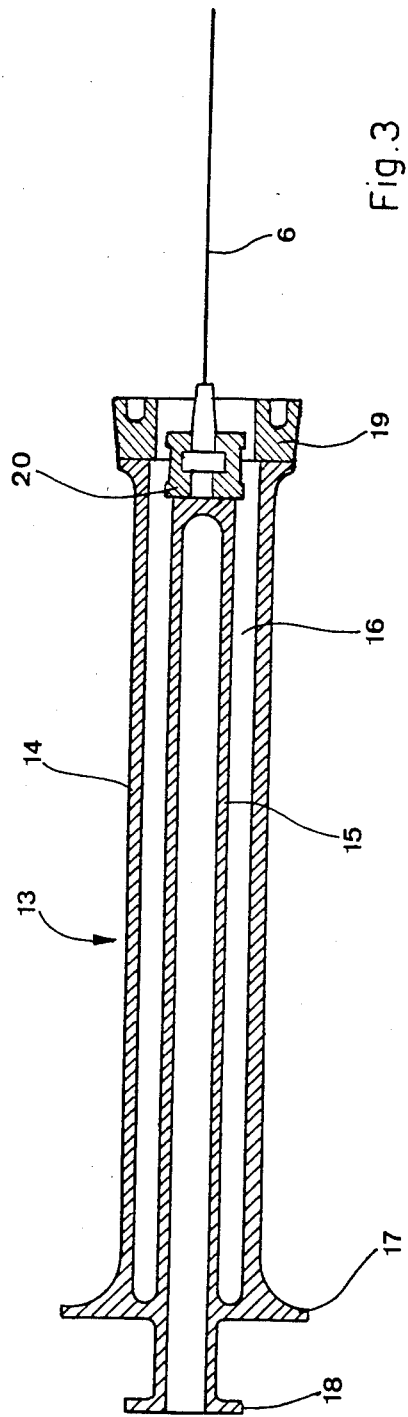
FIG. 3 is a longitudinal and axial section through the syringe plunger.

With reference to the drawings:

1 denotes the syringe body, consisting of an inner and outer coaxial cylindrical elements 2 and 3 united at the syringe fore-end 4 in an integrated shoulder-portion which extends forward to create a truncate-conical seating 5 lying beyond though disposed coaxially with elements 2 and 3, wherein the hypodermic needle's moving core 6 is caused to slide. 7 denotes an ordinary hypodermic needle fitted to truncate-conical seating 5 aforesaid. A first annular chamber 8 exists between cylindrical elements 2 and 3 having one end closed off at fore-end 4, and the remaining end left open. The interior of inner cylindrical element 3 defines a central cylindrical cavity 9—open at either end—which extends into a truncate-conical section 10 and runs thus into seating 5 aforesaid. The end of outer cylindrical element 2 farthest away from syringe-fore-end 4 extends into two elastically-deformable, or flexible lugs 11, each one of which provided with a detent 12.

13 denotes the syringe plunger, comprising two coaxially disposed cylinders 14 and 15, the outer one of which 14 open to the fore and enclosed at the rear by an annular portion 17 uniting plunger cylinder 14 as a whole with the outer wall of inner plunger cylinder 15, the inner cylinder itself being enclosed to the fore whilst the remaining end thereof extends beyond said annular portion 17 to terminate in a disc, or button 18 upon which the user's thumb may rest.

A second annular chamber 16 exists between the outer 14 and the inner 15 plunger cylinders of plunger 13, whose rear end is enclosed by said annular portion 17.

A truncate-conical lip-seal 19 is fitted to the fore end of the plunger 13 on its outer cylinder 14, thus mating in sliding contact with the inner wall of annular chamber 8 offered by the syringe body, and creating an air/fluid-tight seal therewith.

The moving core 6 of hypodermic needle 7 aforementioned is mounted to the plunger's inner cylinder 15 at its foremost end. The base of the moving core 6 is ensheathed by a packing 20 exhibiting an undercut outer profile, this designed to slide within and create an air/fluid-tight seal with the syringe-body's central cylindrical chamber 9.

Figure 4:
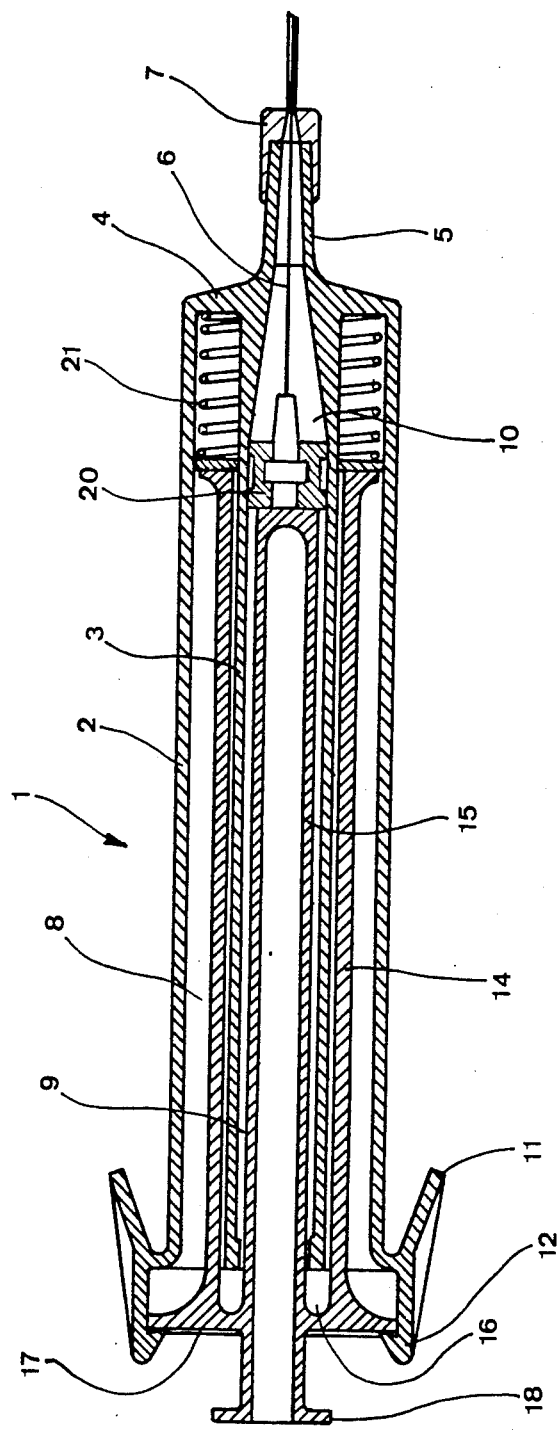
FIG. 4 is a longitudinal, axial section through a syringe embodied as per the invention, furnished with a spring device bringing about return of the plunger.
Figure 5:
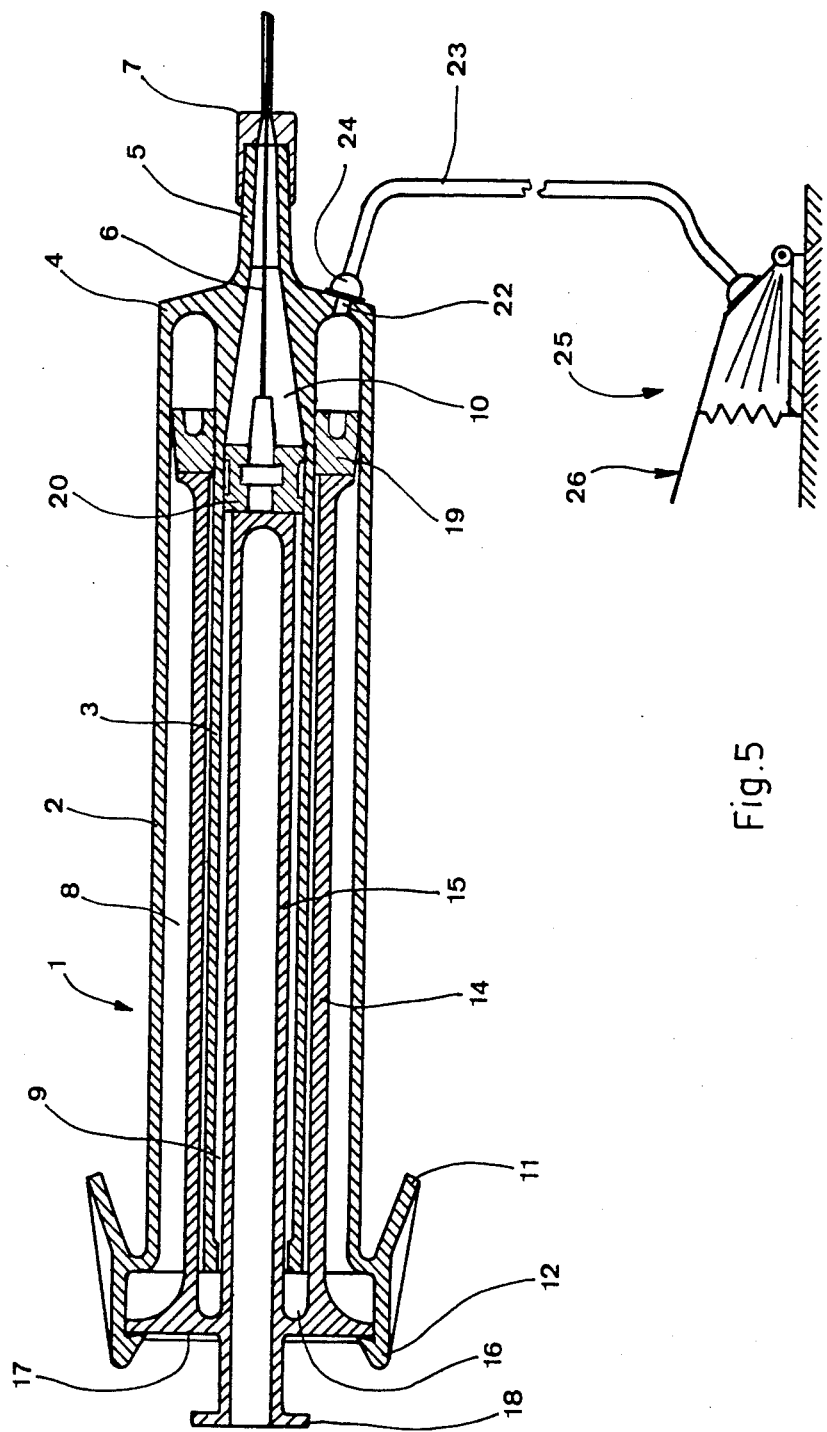
FIG. 5 is the longitudinal and axial section through a syringe incorporating pneumatic or hydraulic plunger-return means—pressurised fluid being fed to the syringe from without.

With reference to FIG. 4: a spring denoted 21—this located at the foremost end of the plunger's 13 outer cylinder 14—replaces the truncate-conical seal 19 in the former embodiment. And referring to FIG. 5: 22 denotes a through hole located in the syringe body 1 at fore-end 4 by way of which pressurised gas or fluid may pass from a rigid free-pipe 23 into annular cavity 8. The pipe itself 23 is connected at one end to said hole 22 by a union 24, its remaining end coupling with whatever manual or automatic means are employed for pumping in said pressurised gas or fluid—these perhaps operated by a pedal 26.

The syringe functions thus:

before inserting the hypodermic needle into whichever part of the patient's body has been selected for the biopsy, the syringe plunger 13 is pressed forward by exerting thumb-pressure on button 18 to the point where annular portion 17 engages the detents 12 offered by lugs 11 and snaps into place. The needle 7 is now inserted to the depth at which a tissue-sample needs to be extracted for analytical purposes. This accomplished, transverse pressure is applied to said lugs 11 so as to free annular portion 17 from the detents 12 and permit the return of plunger 13—this brought about automatically either by the effect of compressed air accumulated within annular chamber 8 of the syringe body 1, or through the action of said spring 21, hitherto compressed.

In the course of plunger 13 making its induced return, the appropriate vacuum will be created within the chamber 10 of the syringe body whereby a small quantity or organic tissue or fluid is drawn up through the hypodermic needle 7. The return-speed of plunger 13 is not constant, in point of fact, but diminishes along with the decrease in pressure within chamber 8, or with the gradual slackening of alternative spring 21. The same re-adjustment takes place inversely within said chamber 10, with the vacuum gradually disappearing. In the event of there being a need for creating a steady vacuum within chamber 9 and 10 for controlled suction—hence a correspondingly controlled plunger return stroke—then fluid or gas may be introduced at constant pressure into annular chamber 8 by way of said hole 22 (see FIG. 5), duly brought in through pipe 23 from the manual or automatic means 25 aforementioned, which may be actuated by the user's working a pedal 26, for example.

We claim:

1. Syringe for hypodermic biopsy incorporating automatic plunger-return and utilizing a hypodermic needle, comprising:

a syringe body having a fore-end and a rear end and including inner and outer coaxial cylindrical elements united integrally at the fore-end of the syringe body and extending thence into a pierced truncate-conical seating lying beyond and disposed coaxially with said cylindrical elements;

a first annular chamber disposed between and defined by said inner and outer cylindrical elements, said chamber having one end enclosed by said syringe fore-end said inner cylindrical cavity located centrally therein, and terminating at its foremost end in a truncate-conical portion which in turn communicates with said seating;

said syringe body housing an axially-movable plunger composed of two coaxial plunger cylinders, the outer plunger cylinder open at its foremost end and enclosed at the remaining rear end by an annular portion; the inner plunger cylinder being enclosed at its foremost end with its rear end extending beyond said annular portion and terminating in a disc; a second annular chamber between said outer plunger cylinder and said inner plunger cylinder the rear end of which is enclosed by said annular portion;

the foremost end of said inner plunger cylinder offering a fixing-point for the moving core of a hypodermic needle; the base of said core being ensheathed by a packing exhibiting an undercut outer profile and designed to slide within said cylindrical cavity, duly creating an airtight and fluidtight seal therewith; further comprising means for applying pressure to the foremost end of said outer plunger cylinder so as to cause said plunger to move, coaxially within said syringe body, away from the fore-end of said syringe body, means, comprising a detent at the rear end of said outer cylindrical element, for preventing said means for applying pressure from causing said plunger to move, coaxially within said syringe body, away from the fore-end of said syringe body by releasably engaging said annular portion, and means for disengaging said annular portion from said detent, so that said means for applying pressure causes said plunger to move coaxially within said syringe body, away from the fore-end of said syringe body.

2. Syringe according to claim 1 wherein said means for applying pressure comprises a truncate-conical lip-seal fitted to the fore-end of the outer plunger cylinder said truncate-conical lip-seal forming an air- and fluid-tight seal between said inner and outer cylindrical elements of said syringe body.

3. Syringe according to claim 1 wherein said means for applying pressure comprises: a spring located forward of the outer plunger cylinder fore-end, in a manner such that said spring may be compressed within said first annular chamber upon insertion of said plunger into the syringe-body.

4. A syringe for hypodermic biopsy incorporating automatic plunger-return and utilizing a hypodermic needle, comprising:

a syringe body having a fore-end and a rear end and including inner and outer coaxial cylindrical elements united integrally at the fore-end of the syringe body and extending thence into a pierced truncate-conical seating lying beyond and disposed coaxially with said cylindrical elements;

a first annular chamber disposed between and defined by said inner and outer cylindrical elements, said chamber having one end enclosed by said syringe fore-end said inner cylindrical element being open at both ends, thereby defining a cylindrical cavity located centrally therein, and terminating at its foremost end in a truncate-conical portion which in turn communicates with said seating;

said syringe body housing an axialy-movable plunger composed of two coaxial plunger cylinders, the outer plunger cylinder open at its foremost end and enclosed at the remaining rear end by an annular portion; the inner plunger cylinder being enclosed at its foremost end with its rear end extending beyond said annular portion and terminating in a disc; a second annular chamber between said outer plunger cylinder and said inner plunger cylinder the rear end of which is enclosed by said annular portion;

the foremost end of said inner plunger cylinder offering a fixing-point for the moving core of a hypodermic needle; the base of said core bing ensheathed by a packing exhibiting an undercut outer profile and designed to slide within said cylindrical cavity, duly creating an airtight and fluidtight seal therewith; further comprising means for applying pressure to the foremost end of said outer plunger so as to cause said plunger to move, coaxially within said syringe body, said syringe further comprising a through hole in the syringe body located at said fore-end of said syringe body, a rigid feed pipe being connected at one end of said through hole and at the other end to means for bringing a pressurized fluid into said first annular chamber.

5. A syringe according to claim 4 wherein said means for applying pressure comprises a truncate-conical lip-seal fitted to the fore-end of the outer plunger cylinder said truncate-conical lip-seal forming air- and fluidtight seal between said inner and outer cylindrical elements of said syringe body.

* * * * *

UNITED STATES PATENT AND TRADEMARK OFFICE
CERTIFICATE OF CORRECTION

PATENT NO. : 4,542,749

DATED : September 24, 1985

INVENTOR(S) : Caselgrandi et al

It is certified that error appears in the above-identified patent and that said Letters Patent is hereby corrected as shown below:

Title page: Item [76] should read as follows:

Inventors: Ivo Caselgrandi, c/o Gardipatent, - 605, Via Giardini, Palazzo Prora; Beniamino Palmieri, 45, Via Boito, both of 41100 Modena, Italy Signed and Sealed this Twenty-fifth Day of February 1986

[SEAL]

Attest:

DONALD J. QUIGG

*Attesting Officer*    *Commissioner of Patents and Trademarks*